(12) United States Patent
Weissmüller et al.

(10) Patent No.: US 6,677,142 B1
(45) Date of Patent: Jan. 13, 2004

(54) POLYSACCHARIDES CONTAINING α-1,4-GLUCAN CHAINS AND METHOD FOR PRODUCING SAME

(75) Inventors: Max Weissmüller, Kriftel (DE); Martin Quanz, Berlin (DE); Nicholas Provart, Berlin (DE)

(73) Assignee: Celanese Ventures GmbH, Frankfurt am Main (DE)

( * ) Notice: Subject to any disclaimer, the term of this patent is extended or adjusted under 35 U.S.C. 154(b) by 0 days.

(21) Appl. No.: 09/869,510

(22) PCT Filed: Nov. 30, 1999

(86) PCT No.: PCT/EP99/09299

§ 371 (c)(1), (2), (4) Date: Aug. 22, 2001

(87) PCT Pub. No.: WO00/39321

PCT Pub. Date: Jul. 6, 2000

(30) Foreign Application Priority Data

Dec. 28, 1998 (DE) .......................................... 198 60 376

(51) Int. Cl.[7] .......................... C12P 19/04; C12P 19/00
(52) U.S. Cl. ......................... 435/101; 435/99; 435/72; 435/97
(58) Field of Search ........................... 435/101, 99, 72, 435/97

(56) References Cited

U.S. PATENT DOCUMENTS 5,229,277 A  7/1993  Day et al. .................... 435/103

FOREIGN PATENT DOCUMENTS

| DE | 197 29 273 A1 | 1/1999 |
| JP | 1997/75745 | 12/1997 |
| WO | WO 95/31553 | 11/1995 |

OTHER PUBLICATIONS

"New Studies on Amylosucrase, a Bacterial α–D–Glucosylase That directly Converts Sucrose to a Glycogen–Like α–Glucan", Okada et al., J. Biol. Chem. 249:126–135 (1974).

"Acceptor Reaction of a Highly Purified Dextransucrase With Maltose and Oligosaccharides. Application to the Synthesis of Controlled–Molecular–Weight Dextrans", F. Paul, Carbohydrate Research, 149 (1986), pp. 433–441.

"Studies on a Recombinant Amylosucrase", Remaud–Simeon et al., Progress in Biotechnology 10, Carbohydrate Bioengineering, Apr. 23–26, 1995, pp. 313–320.

"Glycogen Synthesis by Amylosucrase from Neisseria Perflava", MacKenzie et al., Can. J. Microbiol. vol. 23, 1977, pp. 1303–1307.

International Search Report in PCT/EP99/09299 dated Apr. 26, 2000.

International Preliminary Examination Report in PCT/EP99/09299 dated Apr. 9, 2001.

*Primary Examiner*—Francisco Prats
(74) *Attorney, Agent, or Firm*—Marshall, Gerstein & Borun LLP

(57) ABSTRACT

The invention relates to a method for producing polysaccharides containing α-1,4-glucan chains. According to the inventive method, a glucosyl group acceptor undergoes a chain prolongation reaction by reacting it with saccharose in the presence of an amylosaccharase. The amount of the glucosyl group acceptor in the reaction mixture is chosen in such a way that the mole ratio of the available ends of the glucosyl group acceptor to the saccharose is at least 1:1,000 and/or the weight ratio of the glucosyl group acceptor to the saccharose is at least 1:0.

10 Claims, 2 Drawing Sheets

POLYSACCHARIDES CONTAINING α-1,4-GLUCAN CHAINS AND METHOD FOR PRODUCING SAME

This is the U.S. national phase of International Application No. PCT/EP99/09299 filed Nov. 30, 1999, the entire disclosure of which is incorporated herein by reference.

DESCRIPTION

The present invention relates to α-1,4-glucan-chain-containing polysaccharides and to a process for their preparation.

Polysaccharides are polymers which are composed of numerous glycosidically bound monosaccharides. Polysaccharides occur both in higher organisms and in microorganisms such as bacteria and there fulfill, for example, the function of storage and framework substances. The polysaccharides are used commercially, inter alia, as aids and additives in the food industry, in light industry, in health care and in analysis.

Glucans are polysaccharides which solely consist of glucose monomers. In the α-1,4-glucans, these glucose radicals are linked to one another by α-1,4-glycosidic bonds. α-1, 4-Glucans, owing to their physicochemical properties, can be used to produce films which are color-free, odorless and tasteless, non-toxic and biodegradable. Already, there are numerous applications for such films, for example in the food industry, the textile industry and the glass fiber industry.

The most frequently occurring natural α-1,4-glucan is amylose, a starch constituent. Amylose is already used to produce fibers whose properties resemble those of natural cellulose fibers and make possible their partial or complete replacement in paper making. In pharmacy, amylose is used as a filler for tablets, pastes and as additive to skin protection substances. In the food industry, it serves as thickener and binder for puddings, soups, sauces, mayonnaises, cream fillings and as a gelatin substitute. Amylose is also used as a binder in the production of sound-insulating wall panels.

Amylopectin, the main constituent of starch, and glycogen are further polysaccharides whose main chains consist of glucose radicals having α-1,4-glycosidic linkage. These polysaccharides bear side chains which are linked to the main chain via α-1,6-glycosidic bonds. These polysaccharides are also used to a great extent in industry.

The isolation of α-1,4-glucans such as starch and glycogen from plant and animal organisms is complex and costly and does not always lead to products having reproducible properties. For this reason, bacteria which can produce such glucans have increasingly become the subject of attention.

In most bacteria, polysaccharides are synthesized in a similar manner to in higher organisms, via nucleotide-activated sugars. Thus, in most bacteria, the biosynthesis of glycogen involves three enzymes, that is to say ADP-glucose phosphorylase, which catalyzes the formation of ADP-glucose from glucose-1-phosphate and ATP, glycogen synthase which transfers the glucose from ADP-glucose to the growing glucan chain, and a branching enzyme which introduces α-1,6-links into the linear α-1,4-glucan chain. However, in some bacteria polysaccharide synthesis can also take place without the participation of activated sugars.

One of the bacterial systems which is able to synthesize polysaccharides without the participation of nucleotide sugars has been found in bacteria of the genus Neisseria. In these bacteria, polysaccharides having a similar structure to glycogen are synthesized by the enzyme amylosucrase directly from sucrose, the natural substrate of the enzyme [Okada, G., and E. J. Hehre, J. Biol. Chem. 249:126–135 (1974); MacKenzie, C. R. et al., Can. J. Microbiol. 23:1303–1307 (1977); MacKenzie, C. R. et al., Can. J. Microbiol. 24:357–362 (1978)].

Amylosucrase (sucrose: 1,4-α-glucan 4-α-glucosyltransferase, E. C. 2.4.1.4.) catalyzes the formation of α-1,4-glycosidically linked glucans, by transferring the glucosyl radical of the sucrose molecule to the growing polymer chain, with the release of D-fructose, according to the following reaction equation

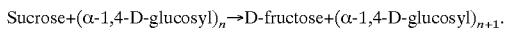

Sucrose+(α-1,4-D-glucosyl)$_n$→D-fructose+(α-1,4-D-glucosyl)$_{n+1}$.

Nucleotide-activated sugars or cofactors are not required in this reaction. However, the enzyme is stimulated by the presence of glucosyl group acceptors (or primers), for example oligo- and polysaccharides such as amylose or glycogen, to which the glucosyl radical of the sucrose is transferred according to the above reaction equation with α-1,4-glucan chain extension [Okada, G., and E. J. Hehre, J. Biol. Chem. 249:126–135 (1974); Remaud-Simeon, M. et al., In S. B. Petersen, B. Svenson and S. Pedersen (editors), Carbohydrate bioengineering, pp. 313–320 (1995); Elsevier Science B. V., Amsterdam, Netherlands].

Amylosucrases have been found to date only in bacteria of the genus Neisseria. The enzyme which is expressed constitutively in the bacteria, is extremely stable and binds very firmly to its polymerization product. In most species investigated the enzyme is localized intracellularly, but in *Neisseria polysaccharea*, the amylosucrase is secreted. The gene for amylosucrase from *Neisseria polysaccharea* has in the interim been isolated and expressed using genetic engineering methods. It has been found that the enzyme highly probably only catalyzes the formation of linear α-1,4-glucan chains (WO 95/31553).

The use of amylosucrase from *N. polysaccharea* for preparing linear α-1,4-glucans has already been proposed in WO 95/31553. However, a problem in the use of amylosucrases for producing polysaccharides is that the polysaccharides usually formed in the presence of amylosucrase have highly variable molecular weights, i.e. a high polydispersity or broad molecular weight distribution. However, for an industrial application, because of their more homogeneous physicochemical properties, polysaccharide preparations having a molecular weight as uniform as possible, that is to say low polydispersity, are desired.

The object of the present invention was therefore to provide α-1,4-glucan-chain-containing polysaccharides having a low polydispersity.

This object was achieved by the processes and polysaccharides described in the claims.

The present invention therefore relates to a process which comprises a glucosyl group acceptor being subjected to a chain extension reaction by reaction with sucrose in the presence of an amylosucrase, the amount of glucosyl group acceptor in the reaction mixture being chosen so that the molar ratio of glucosyl group acceptor ends available for chain extension to sucrose is at least 1:1 000 and/or the weight ratio of glucosyl group acceptor to sucrose is at least 1:50.

The invention also relates to a process which comprises subjecting a glucosyl group acceptor to a chain extension reaction by reaction with sucrose in the presence of an amylosucrase and with addition of fructose.

α-1,4-Glucan-chain-containing polysaccharides which are available by these processes are also subject-matter of this invention.

The inventively used glucosyl group acceptors are compounds on which synthesis of α-1,4-glucan chains, that is α-1,4-glucan chain extension, can proceed under amylosucrase-catalyzed transfer of α-D-glucosyl radicals originating from sucrose. Suitable glucosyl group acceptors are, in particular, short-chain and longer-chain oligo- and polysaccharides having terminal glucose radicals which are linked via α-1,4-glycosidic bonds. Preferably, the inventively used glucosyl group acceptor is an unbranched, particularly preferably a branched, oligo- or polysaccharide. Examples of inventive glucosyl group acceptors are maltooligosaccharides such as maltopentaose, maltohexaose or maltoheptaose.

Preferred glucosyl group acceptors are dextrins, amylopectins, amyloses and amylose-like polysaccharides, for example from corn and potatoes, and glycogens and glycogen-like polysaccharides, for example from muscle tissue, mussels or bacteria.

Particularly preferred glucosyl group acceptors are branched polysaccharides such as glycogen. Such branched glucosyl group acceptors have more than one end at which chain extension can take place. Thus the glycogen chain bears approximately 7–12% of branches to which glucosyl radicals can be transferred.

Surprisingly, it has now been found that, in the amylosucrase-catalyzed synthesis of α-1,4-glucans, polysaccharides having low polydispersity can be obtained if the molar ratio of glucosyl group acceptor ends available for chain extension to sucrose and/or the weight ratio of glucosyl group acceptor to sucrose in the reaction mixture assumes a defined minimum value. The chain extension reaction is presumed to be preferred at this minimum value to side reactions which cause polysaccharide preparations of high polydispersity. The polydispersity, at a constant sucrose concentration, shows a tendency to decrease with increasing concentration of the acceptor.

Expediently, the molar ratio of glucosyl group acceptor ends available for chain extension to sucrose in the reaction mixture is at least 1:1000. Preferably, the molar ratio is at least 5:1000, and particularly preferably at least 1:100. The upper limit for the molar ratio of glucosyl group acceptor ends available for chain extension to sucrose is not very critical and is expediently approximately 1:50 to 1:25.

The weight ratio of glucosyl group acceptor to sucrose is expediently at least 1:50, for example at least 2:50, or at least 5:50. The optimum weight ratio depends on the type of acceptor. In the case of branched polysaccharide acceptors, the amount of acceptor required in the reaction mixture at a given sucrose concentration is generally lower than in the case of unbranched or only slightly branched polysaccharide acceptors. Thus, when glycogen having a weight-average molecular weight $M_w$ of approximately 160 000 g/mol is used, a ratio of acceptor to sucrose of at least 2.5:50 has proved to be advantageous, while in the case of dextrins having an $M_w$ of approximately 5 000 to 6 000 g/mol, a weight ratio of acceptor to sucrose of at least 5:50 to 10:50 is preferred.

For a given sucrose concentration and a given glucosyl group acceptor, the molecular weight of the polysaccharide obtained by the inventive process is lower, the higher the concentration of glucosyl group acceptor chosen. In this manner, by suitable choice of the weight ratio of glucosyl group acceptor to sucrose, the molecular weight of the end product can also be controlled.

The absolute concentration of the sucrose used as substrate of the amylosucrases in the reaction mixture is not critical. The amount used, however, expediently does not exceed 50% (w/v), since, above this concentration, the solution viscosity is too high and the reaction rate sharply decreases. Preferably, the sucrose concentration in the reaction mixture is between 1 and 30% (w/v).

The optimum conditions for the chain extension reaction, for example molar ratio of glucosyl group acceptor ends available for chain extension to sucrose, weight ratio of glucosyl group acceptor to sucrose and sucrose concentration in the reaction mixture, may be determined without problem by simple experiments.

It has further been found that in the amylosucrase-catalyzed synthesis of α-1,4-glucans, polysaccharides having low polydispersity may be obtained when fructose is added to the reaction mixture. Presumably, addition of fructose inhibits interfering side reactions which give rise to polysaccharide preparations of high polydispersity. The effect introduced by the presence of fructose is observed independently of whether the molar ratios and weight ratios of glucosyl group acceptor to sucrose have the above-specified minimum values or not. The addition of fructose leads to a still narrower molecular weight distribution, that is to a smaller polydispersity of the resultant end product, but in exchange the yield is somewhat lower.

Expediently, fructose is added to the reaction mixture at a concentration of at least 10 mM. Preferably, the fructose is added at a concentration of at least 50 mM, preferably 100 to 800 mM.

By means of the inventive process, an increase in the molecular weight of the glycosyl group acceptor used to twice to three times may be achieved, without problems. The molecular weight of the acceptor used in the inventive process therefore also depends on the desired molecular weight of the end product. Since the reaction rate of the chain extension reaction increases with increasing degree of polymerization of the acceptor, expediently, however, acceptors having a weight-average molecular weight $M_w$ of at least $0.5 \times 10^3$ g/mol, preferably at least $4 \times 10^3$ g/mol, and particularly preferably at least $1 \times 10^5$ to $1 \times 10^6$ g/mol, are used. Since the polydispersity of the resultant reaction products is also impaired by the uniformity of the acceptor material used, it is also advisable to use acceptor molecules having the lowest possible polydispersity.

All enzymes can be used as amylosucrases which are able, according to the reaction equation $$\text{Sucrose} + (\alpha\text{-1,4-D-glucosyl})_n \rightarrow \text{D-fructose} + (\alpha\text{-1,4-D-glucosyl})_{n+1}$$

to transfer the glucosyl radical of a sucrose molecule to the acceptor molecule with release of D-fructose and formation of an α-1,4-glucan chain. Preferably, amylosucrases from prokaryotes are used, in particular from bacteria of the genus Neisseria. Suitable amylosucrases are those occurring, for example, in the bacterial species *N. sicca, N. canis, N. cinerea, N. perflava, N. subflava, N. dentrificans* and *N. polysaccharea*. Preferably, amylosucrase from *N. polysaccharea* is used, for example from *N. polysaccharea* ATCC 43768.

The amylosucrases used can either be isolated directly from the organisms in which they are naturally synthesized (MacKenzie, C. R. et al., Can. J. Microbiol., 24: 357–362; 1978), or, as described in WO 95/31553, they can be produced by genetic engineering methods (recombinant amylo-sucrases). The enzymes can also be produced in cell-free conditions using in vitro transcription and translation systems.

The amylosucrases can be used not only as crude enzymes or in partially purified form, but also in highly purified form. Preferably, highly purified amylosucrases are used, the term "highly purified amylosucrase" being taken to mean in particular an amylosucrase having a purity of at least 80%, preferably at least 90%, and particularly preferably at least 95%.

The use of highly purified amylosucrases in the inventive process has the advantage that the enzymes do not contain residues of the strain, for example the microorganism, from which they were isolated. For example, highly purified preparations do not contain other unwanted enzymes, for example polysaccharide-degrading enzymes such as amylases. The use of highly purified amylosucrases is also advantageous for use in the food industry and pharmaceutical industry, since a reaction medium which is defined and free from unnecessary constituents also gives a more precisely defined product. This leads to less complex authorization processes for these biotechnologically produced products in the food industry and pharmaceutical industry, in particular if these products are not to have any traces of transgenic microorganisms.

Preferably, recombinant amylosucrases are used as described, for example, in WO 95/31553. Such recombinant amylosucrases can be genetically modified with respect to the naturally occurring amylosucrases, if appropriate also by mutations, for example insertions, deletions and substitutions, in order to modify defined properties of the expressed protein. Thus, the amylosucrase can, for example, be expressed as a fusion protein together with a polypeptide sequence whose specific binding properties enable easier isolation of the fusion protein, for example by affinity chromatography (see, for example, Hopp et al., Bio/Technology 6 (1988), 1204–1210; Sassenfeld, Trends Biotechnol. 8 (1980), 88–93). Particularly preferably, amylosucrases are used which are secreted by the host cells into the nutrient medium, so that cell digestion and further purification of the enzyme are not necessary, because the secreted enzyme can be obtained from the supernatant. The amylosucrase can, as in the case of *N. polysaccharea* be secreted naturally, or secretion can be achieved by the enzyme being expressed together with a signal peptide, with the aid of which the enzyme can pass through the cell membrane of the host organism.

The amylosucrase can be used in free form or immobilized to a support material. Immobilization of the amylosucrase offers the advantage that the enzyme can be recovered in a simple manner from the reaction medium and used repeatedly. Since the purification of enzymes is generally costly and time-consuming, immobilization and reuse of the enzyme permits considerable cost savings. A further advantage is the purity of the reaction products, which contain no protein residues. Suitable support materials are, for example, agarose, alginate, cellulose, polyacrylamide, silica or nylon, with the coupling to the support material being via covalent or noncovalent bonds.

The amount of amylosucrase used is usually between 0.1 and 100 U/ml, preferably between 1 and 50 U/ml, and particularly preferably between 2 and 25 U/ml.

The inventive polysaccharides are expediently prepared in vitro in buffer-free or buffered aqueous systems having a pH between 4 and 9, preferably between 5.5 and 7.5. Suitable buffer systems are, for example, citrate buffer, maleate buffer and acetate buffer.

The reaction temperature is expediently between 10 and 60° C., preferably between 25 and 45° C.

The reaction is expediently carried out up to complete conversion of the sucrose. Usually, the reaction time for this is between 1 and 150 hours, for example between 10 and 100 hours.

The inventively formed polysaccharides are frequently sparingly soluble in water and may therefore be separated off from the reaction mixture without difficulty, for example by centrifugation. Water-soluble or partially water-soluble polysaccharides can be isolated, for example, by precipitation with ethanol or by freezing out.

The inventive processes permit a simple and inexpensive preparation of α-1,4-glucan-chain-containing polysaccharides of low polydispersity. The processes are distinguished by an easy controllability of the molecular weight of the end products by an outstanding reproducibility. This makes it possible to prepare products of constant uniformity and purity and therefore of high quality, which is of great importance for further industrial use. The resultant products may be worked up inexpensively, since the process parameters which are required for the work up do not need to be optimized anew for each work up batch.

DESCRIPTION OF THE DRAWINGS

The inventive process is useful in controlling the molecular weight during the preparation of polysaccharides. In one embodiment, the inventive α-1,4-glucan-chain-containing polysaccharides are useful as tablet fillers.

Figure 1:
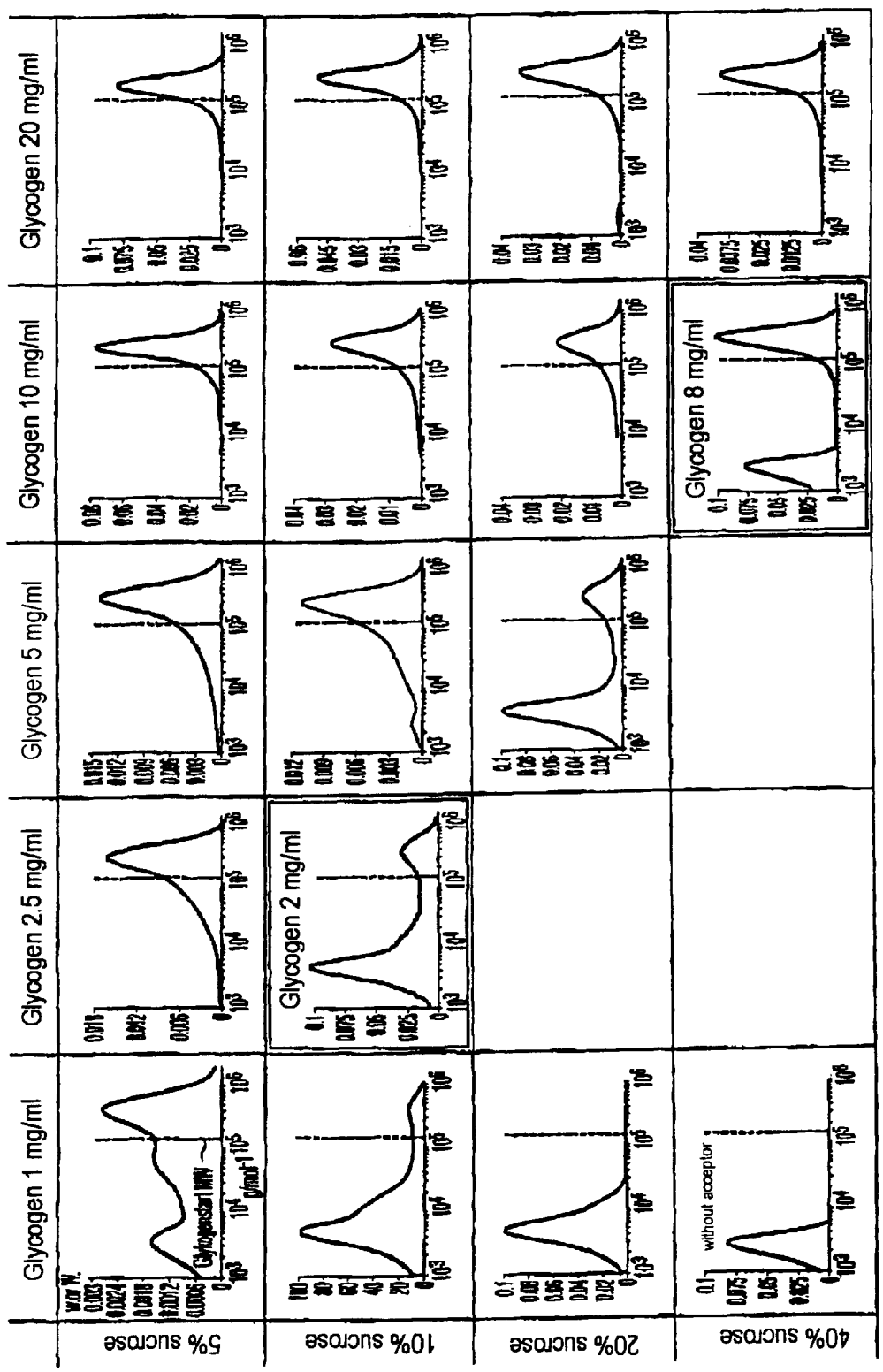
FIG. 1 shows the molecular mass distribution of α-1,4-glucan-chain-containing polysaccharides in the reaction of glycogen as glucosyl group acceptor with sucrose in the presence of amylosucrase as a function of the glycogen concentration and sucrose concentration.

The present invention is described in more detail by the examples below.

EXAMPLE 1

Purification of Amylosucrase

To produce amylosucrase, *E. coli* cells were used which had been transformed with the vector pNB2 containing an amylosucrase from *Neisseria polysaccharea* (WO 95/31553).

An overnight culture of these *E. coli* cells which secrete the amylosucrase from *Neisseria polysaccharea* was centrifuged and the cells were resuspended in approximately 1/20 of the volume of 50 mM sodium citrate buffer (pH 6.5), 10 mM DTT (dithiothreitol), 1 mM PMSF (phenylmethylsulfonyl fluoride). The cells were then disintegrated twice using a French press at 16 000 psi. Then 1 mM $MgCl_2$ and benzonase (Merck; 100 000 units; 250 units $\mu l^{-1}$) at a final concentration of 12.5 units $ml^1$ were added to the cell extract. The mixture was then incubated for at least 30 min with gentle stirring at 37° C. The extract was allowed to stand on ice for at least 1.5 hours. It was then centrifuged for 30 min at approximately 40 000 g until the supernatant was relatively clear. Prefiltration via a PVDF membrane (Millipore "Durapore", or similar) having a pore diameter of 0.45 $\mu m$ was carried out. The extract was allowed to stand overnight at 4° C. To carry out hydrophobic interaction (HI) chromatography, solid NaCl was added to the extract and a concentration of 2 M NaCl was set. The mixture was again centrifuged for 30 min at 4° C. and approximately 40 000 g. The extract was then freed from the final residues of E. coli by filtering it through a PVDF membrane (Millipore "Durapore" or similar) which had a pore diameter of 0.22 μm. The filtered extract was separated on a butylsepharose-4B column (Pharmacia) (column volume: 93 ml, length: 17.5 cm). Approximately 50 ml of extract having an amylosucrase activity of 1 to 5 units$^{-1}$ were added to the column. Non-binding proteins were then washed from the column with 150 ml of buffer B (buffer B; 50 mM sodium citrate pH 6.5, 2 M NaCl). The amylosucrase was then eluted using a decreasing linear NaCl gradient (from 2 M to 0 M NaCl in 50 mM sodium citrate in a volume of 433 ml at a flow rate of 1.5 ml min$^{-1}$), which was generated using an automatic pump system (FPLC, Pharmacia). The amylosucrase was eluted between 0.7 M and 0.1 M NaCl. The fractions were collected, desalted via a PD10-Sephadex column (Pharmacia), stabilized with 8.7% glycerol, tested for amylosucrase activity and then frozen in storage buffer (8.7% glycerol, 50 mM citrate).

EXAMPLE 2
Determination of Amylosucrase Activity

Purified protein or crude protein extract was added at various dilutions to 1 ml assay solutions containing 5% sucrose, 0.1% glycogen and 100 mM citrate, pH 6.5, and incubated at 37° C. After 5 min, 10 min, 15 min, 20 min, 25 min, and 30 min, 100 μl were removed from this assay solution each time and the amylosucrase enzymatic activity was stopped by [imMediate] immediate heating for 10 min at 95° C. Using a coupled enzyme test, the amount of fructose released from sucrose by the amylosucrase was determined photometrically (M. Stitt et al., Methods in Enzymology 174:518–552; (1989). For this, 1 μl to 10 μl of the inactivated sample are added to 1 ml of 50 mM imidazole buffer pH 6.9, 2 mM MgCl$_2$, 1 mM ATP, 0.4 mM NAD and 0.5 U/ml of hexokinase. After sequential addition of glucose-6-phosphate dehydrogenase (from Leukonostoc mesenteroides) and phosphoglucose isomerase, the change in absorption at 340 nm was measured. The amount of glucose released was then calculated using the Lambert-Beer law. If the result obtained is related to the time point of sampling, the number of enzyme units U may be determined.

1U was defined as the amount of amylosucrase which, under the abovementioned conditions, releases 1 μmol of fructose/min.

EXAMPLE 3
Preparation of Polysaccharides 3.1 To prepare polysaccharide preparations, amylosucrase in 10 ml of 0.1 M sodium acetate buffer, pH 6.5, 0.02% sodium azide was incubated at 37° C. with various concentrations of glycogen (Merck; $M_w$, 160 000, polydispersity approximately 1.4) as glucosyl group acceptor and sucrose as substrate up to complete conversion of the sucrose, i.e. at least 48 hr. The amylosucrase was added at a concentration of 5 to 20 U/ml. A parallel control sample without glycogen was treated under otherwise identical conditions.

The polysaccharide precipitated out was centrifuged off (15 min, 1200 g) and washed twice by resuspension in water and repeated centrifugation. The pellets were frozen at −20° C. and freeze-dried at 0.34 mbar and an ambient temperature of 25° C. (Alpha 1.4 freeze drier, Christ). The sample temperature during drying was −25° C.

The resultant products were analyzed by gel permeation chromatography (GPC).

The operations were carried out as specified in DIN 55672-1. All measurements were carried out in dimethyl sulfoxide (DMSO) using 0.09 M NaNO$_3$ as eluent. The GPC used a column combination of PS gel columns (10$^3$, 10$^5$ and 10$^6$ Å; from PSS, Mainz, type "SDV 10 μ"). For detection of the mass fractions, a differential refractometer from Shodex, type "RI 71" was used. A pump from Bischoff, type "HPLC Compact Pump" was used. The flow rate was 1 ml/min. Linear pullulans from PSS, Mainz, were used for calibration. (Since the samples had branched structures, the measured results are not absolute but relative sizes, which, however, are comparable within a constant degree of branching of the samples.) The GPC software from PSS "Win-GPC scientific 4.02" was completely in compliance with DIN 55672-1 and was fully validated. The correctness of the data processing steps was therefore reproducible independently of the system. Molar masses having values less than 1000 g/mol were not taken into consideration in the evaluation.

The results are listed in the table below and are shown graphically in FIG. 1 ($w_i$ and $W_i$ designate the normalized and relative mass fractions of the ith polymer fraction). The perpendicular dotted line shows the initial molecular weight of the glycogen used as glucosyl group acceptor.

The results show that the polydispersity of the resultant polysaccharides decreases drastically with constant sucrose concentration and increasing glycogen concentrations.

TABLE

| Glycogen mg/ml | Sucrose (%) | | | | | | | | | | | |
|---|---|---|---|---|---|---|---|---|---|---|---|---|
| | 5 | | | 10 | | | 20 | | | 40 | | |
| | $M_w$ | $M_n$ | $I_n$ | $M_w$ | $M_n$ | $I_n$ | $M_w$ | $M_n$ | $I_n$ | $M_w$ | $M_n$ | $I_n$ |
| 0 | 67 170 | 2 129 | 32 | 7 248 | 1 953 | 3.7 | 4 210 | 1 215 | 3.5 | 2 082 | 9 24 | 2.3 |
| 1 | 224 400 | 17 460 | 13 | 101 700 | 7 894 | 13 | 11 250 | 2 811 | 4 | | | |
| 2.5 | 251 400 | 28 080 | 9 | 95 670 | 4 701 | 20 | | | | | | |
| 5 | 315 300 | 71 650 | 4.4 | 248 500 | 24 785 | 10.7 | 113 300 | 5 580 | 21.5 | | | |
| 10 | 303 500 | 235 600 | 1.3 | 316 900 | 76 380 | 4.1 | 247 900 | 12 380 | 20 | 200 700 | 5 069 | 40 |
| 20 | 244 100 | 195 800 | 1.3 | 317 000 | 243 600 | 1.3 | 319 400 | 40 580 | 7.9 | 277 800 | 20 090 | 14 |

$M_w$ Weight-average molecular weight
$M_n$ Number-average molecular weight
$I_n$ Polydispersity ($M_w/M_n$)

Figure 2:
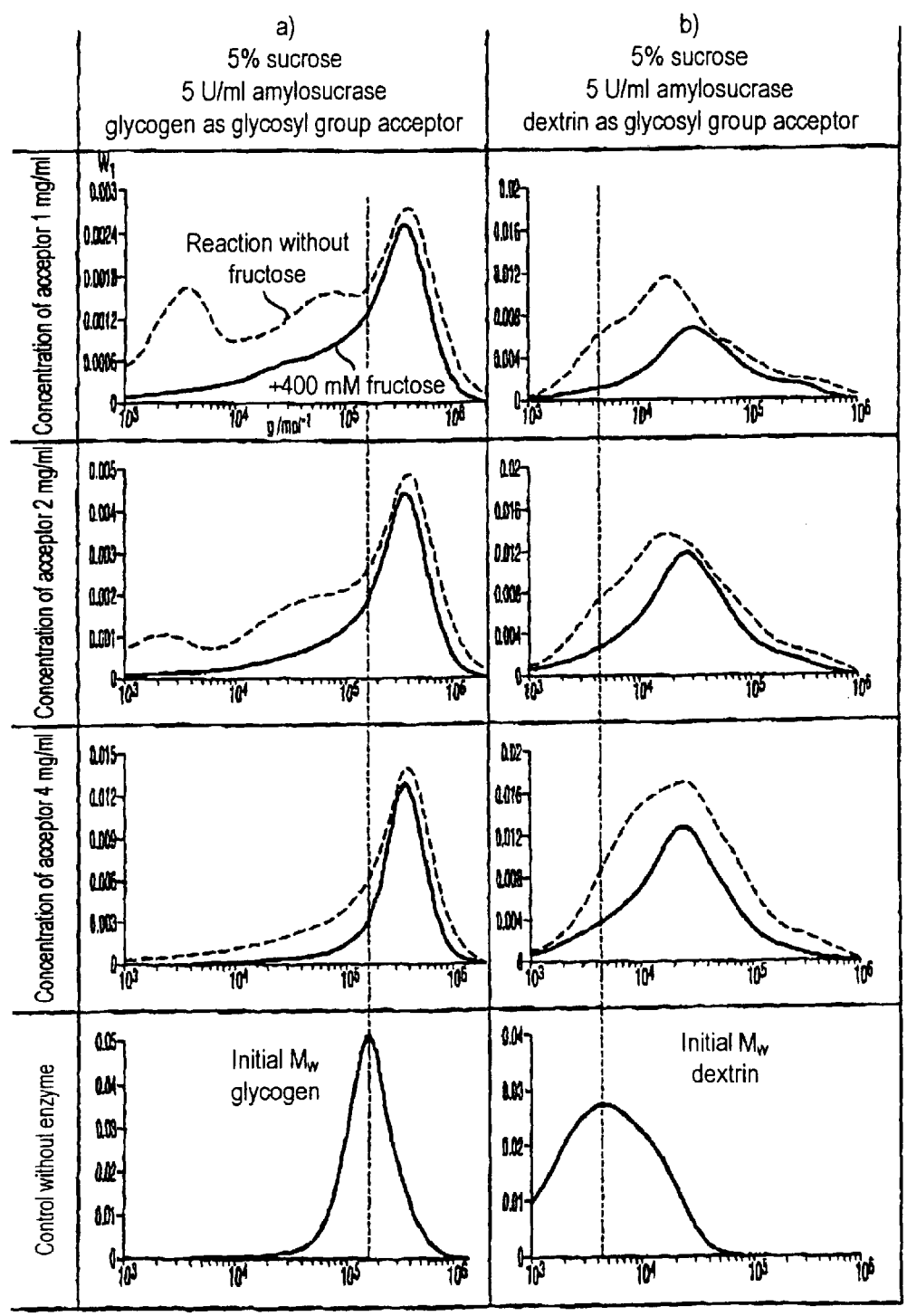
FIG. 2a shows the molar mass distribution of α-1,4-glucan-chain-containing polysaccharides in the reaction of glycogen with sucrose in the presence of amylosucrase as a function of the glycogen concentration and sucrose concentration in the presence and absence of fructose.
FIG. 2b shows the molar mass distribution of α-1,4-glucan-chain-containing polysaccharides in the reaction of dextrin with sucrose in the presence of amylosucrase as a function of dextrin concentration and sucrose concentration in the presence and absence of fructose.

3.2 In a further experiment, amylosucrase (5 U/ml) in 10 ml of 0.1 M sodium acetate buffer, pH 6.5, 0.02% sodium azide, 5% sucrose (w/v) was incubated at 37° C. with glycogen at various concentrations and in the presence of fructose (initial concentration 400 mM) or without fructose to complete conversion of the sucrose (at least 48 hr). A parallel control sample without enzyme was treated under otherwise identical conditions. The resultant polysaccharide products were centrifuged off as described under 3.1, washed, freeze-dried and analyzed by GPC. The results are shown graphically in FIG. 2a, in which $W_i$ has the meaning mentioned above. The vertical dotted line shows the initial molecular weight of the glycogen used as glucosyl group acceptor.

The results show that the polydispersity of the resultant polysaccharides decreases with constant sucrose concentration and increasing glycogen concentration. In the presence of fructose, a further decrease in polydispersity is observed.

3.3 The experiment described under 3.2 was repeated under identical conditions, but instead of glycogen, dextrin (Sigma No. D-4894, type IV from potatoes, $M_w$ 6 650) was used. After incubation at 37° C. to complete conversion of sucrose (at least 48 hr) in the presence and absence of fructose, the resultant polysaccharides were centrifuged off as described above, washed and freeze-dried. A parallel control sample without enzyme was treated under otherwise identical conditions and worked up and analyzed as described above. The results are shown graphically in FIG. 2, in which $W_I$ has the meaning mentioned above. The vertical dotted line shows the initial molecular weight of the dextrin used as glucosyl group acceptor.

The results show that the polydispersity of the resultant polysaccharides decreases with constant sucrose concentration and increasing dextrin concentrations. In the presence of fructose, a further decrease in polydispersity is observed.

What is claimed is:

1. A process for preparing α-1,4-glucan-chain-containing polysaccharides, comprising the step of subjecting a glucosyl group acceptor to a chain extension reaction by reacting said glucosyl group acceptor with sucrose in the presence of an amylosucrase and with addition of fructose in a reaction mixture, said fructose being added to the reaction mixture at a concentration of 100 mM to 800 mM, the amount of glucosyl group acceptor in the reaction mixture being selected such that the molar ratio of glucosyl group acceptor ends available for chain extension to sucrose is at least 1:1000 and/or the weight ratio of glucosyl group acceptor to sucrose is at least 1:50.

2. The process of claim 1, wherein the molar ratio of glucosyl group acceptor ends available for chain extension to sucrose is at least 5:1000.

3. A process for preparing α-1,4-glucan-chain-containing polysaccharides, which comprises subjecting a glucosyl group acceptor to a chain extension reaction by reaction with sucrose in the presence of an amylosucrase and with addition of fructose in a reaction mixture, wherein the fructose is added to the reaction mixture at a concentration of 100 mM to 800 mM.

4. The process of claim 3, wherein the amylosucrase used is an amylosucrase from bacteria of the genus Neisseria.

5. The process as claimed in claim 4, wherein the amylosucrase used is an amylosucrase from bacteria of the species *Neisseria polysaccharea*.

6. The process of claim 3, wherein the glucosyl group acceptor used is selected from the group consisting of dextrins, amylose, amylopectin and glycogen.

7. The process of claim 1, wherein the molar ratio of glucosyl group acceptor ends available for chain extension to sucrose is at least 1:100.

8. The process of claim 1, wherein the amylosucrase used is an amylosucrase from bacteria of the genus Neisseria.

9. The process of claim 8, wherein the amylosucrase used is an amylosucrase from bacteria of the species *Neisseria polysaccharea*.

10. The process of claim 1, wherein the glucosyl group acceptor used is selected from the group consisting of dextrins, amylose, amylopectin and glycogen.

* * * * *